United States Patent
Thewes

(10) Patent No.: US 6,856,161 B2
(45) Date of Patent: Feb. 15, 2005

(54) SENSOR ARRAY AND METHOD FOR DETECTING THE CONDITION OF A TRANSISTOR IN A SENSOR ARRAY

(75) Inventor: Roland Thewes, Grobenzell (DE)

(73) Assignee: Infineon Technologies AG (DE)

( * ) Notice: Subject to any disclaimer, the term of this patent is extended or adjusted under 35 U.S.C. 154(b) by 0 days.

(21) Appl. No.: 10/239,438

(22) PCT Filed: Mar. 29, 2001

(86) PCT No.: PCT/DE01/01239

§ 371 (c)(1),
(2), (4) Date: Feb. 24, 2003

(87) PCT Pub. No.: WO01/75462

PCT Pub. Date: Oct. 11, 2001

(65) Prior Publication Data

US 2003/0155942 A1 Aug. 21, 2003

(30) Foreign Application Priority Data

Mar. 30, 2000 (DE) .......................................... 100 15 958

(51) Int. Cl.[7] .............................................. G01R 31/26
(52) U.S. Cl. ................................... 324/769; 324/158.1
(58) Field of Search ............................... 324/765–770, 324/158.1, 530

(56) References Cited

U.S. PATENT DOCUMENTS

| | | | |
|---|---|---|---|
| 4,568,444 A | | 2/1986 | Nakamura |
| 4,737,854 A | * | 4/1988 | Tandon et al. ............... 358/482 |
| 5,489,846 A | * | 2/1996 | Li et al. ....................... 324/252 |
| 6,154,580 A | | 11/2000 | Kuriyama |
| 6,331,274 B1 | * | 12/2001 | Ackley et al. .............. 422/68.1 |

FOREIGN PATENT DOCUMENTS

| | | |
|---|---|---|
| DE | 3513617 C2 | 3/1988 |
| DE | 19856295 A1 | 9/1999 |
| EP | 0310 230 A2 | 4/1989 |
| JP | 11 044587 A | 2/1999 |

OTHER PUBLICATIONS

L. Bousse et al., "A Process for the Combined Fabrication of Ion Sensors and CMOS Sensors" in IEEE Electron Device Letters, vol. 9, No. 1, pp. 44–46, Jan. 1998.

W.J. Parak, et al., "The field–effect–addressable potentiometric sensor/stimulator (FAPS)—a new concept for a surface potential sensor and stimulator with spatial resolution" In Sensors and Actuators B, Chemical, Elsevier Science, pp. 497–504, 1999, no month.

R. Weis and P. Fronherz, "Frequency dependent signal transfer in neuron transistors" In Physical Review E, pp. 877, 1997, no month.

W. Baumann et al., "Microelectronic Sensor System for microphysiological application on living cells" In Sensors and Actuators B, pp. 77, 1999, no month.

* cited by examiner

*Primary Examiner*—Minh N. Tang
(74) *Attorney, Agent, or Firm*—Altera Law Group, LLC; Jeffrey R. Stone

(57) ABSTRACT

A sensor array is provided including transistors that are coupled together. The transistors are designed as sensors and wherein the sensor array has switching devices for selecting a transistor and wherein the selected transistor's condition may be detected. The sensor array is set up so that the selected transistor is driven as a source follower and at least some of the transistors are MOS field effect transistors that are configured so that at least some of the transistors are capable of detecting biological material.

15 Claims, 15 Drawing Sheets

SENSOR ARRAY AND METHOD FOR DETECTING THE CONDITION OF A TRANSISTOR IN A SENSOR ARRAY

BACKGROUND OF THE INVENTION

The invention concerns a sensor array and a method for detecting a condition of a transistor in a sensor array.

DESCRIPTION OF THE RELATED PRIOR ART

Such a sensor array and such a method are known from [5].

In the sensor array known from [5], MOS field effect transistors are provided, which are arranged in a matrix having N rows and M columns, and coupled together via column connections and row connections respectively. The column connections and/or row connections are usually electrically conducting connections. In addition, a means of selection is provided for selecting a field effect transistor whose condition is to be detected.

In the sensor array known from [5], the field effect transistors are designed as sensors, i.e. they detect a signal to be detected, for example by means of a varying gate potential of the field effect transistor concerned.

When a field effect transistor is selected and its condition is read, the sensor array determines a non-linear characteristic of the curve of the voltage present between the source and drain of the respective field effect transistor. The curve of the voltage that is read is non-linear.

Considerable problems arise in the practical application of the known sensor array as a result of this non-linearity.

In particular, in sensor arrays that are meant to achieve a high spatial resolution, for example in sensor arrays having a very large number of several thousand to several million field effect transistors, each arranged with a mutual separation of 5 $\mu$m or less, huge reliability problems arise with regard to the condition to be detected for the selected transistor. In other words, the reliability problems are to be observed in particular when the ratio of the dimension of the sensor array to the number of field effect transistors held in the sensor array is very low.

This means that for an increasing spatial resolution of the sensor array for a constant or even increasing total area of the sensor array, or correspondingly for a constant spatial resolution and for an increasing total area of the sensor array, considerable reliability problems arise when detecting bioelectric signals.

In addition, the technology used in [5] is very complicated and expensive to manufacture, and is barely compatible with common standard industrial manufacturing processes.

In addition, it is known how to modify MOS field effect transistors so that they can be used as sensors.

In such a field effect transistor, the control of the channel, or rather the control of the density of the charge carriers in the channel region by means of the object or medium to be characterized by the sensor, is performed in such a way that the object or medium influences the potential on the surface of the dielectric lying above the channel region, and changes the condition of the field effect transistor concerned. The condition of the field effect transistor is read via the source contacts and drain contacts.

In normal, non-modified MOS field effect transistor circuit configurations, for example in a standard memory array of transistors in the form of a matrix (e.g. a random access memory (RAM)), the condition of a field effect transistor is modified and read via the source contacts and drain contacts.

An example of a field effect transistor modified in such a way is shown in FIG. 2.

The field effect transistor 200 has a substrate 201, a source region 202, a drain region 203, a channel region 204 and an insulator dielectric 205 specially adapted to applications of biosensor or bioelectronics technology. For biosensor or bioelectronics applications, a cell 206 made of biological material is arranged above the insulator dielectric 205.

As has been described in [2] and [3], with the aid of such a field effect transistor 200, neural signals from the cell 206 made of biological material, which manifest themselves in the form of changes in potential at the cell wall 207 of the cell 206, can be detected and characterized. This is possible because the changes in potential at the cell wall 207 control and modulate the channel current made up of the charge carriers in the field effect transistor 200, or rather the density of the charge carriers present in the channel region 204 of the field effect transistor 200.

Such a field effect transistor 200 is set up so that metabolic products from the cell 206 do not damage the field effect transistor 200 and do not modify its properties.

Furthermore, the sensor materials used in the field effect transistor 200, that lie in contact with the cell 206, have no effect on the metabolism of the cell 206 nor its function, and have no toxic effect on the cell 206.

A further field effect transistor 300, shown in FIG. 3, known as an ion-sensitive field effect transistor, is normally used to find a pH value of a solution under investigation. In general, the ion-sensitive field effect transistor 300 can also be used in gas sensor technology. The field effect transistor 300 has a substrate 301, a source region 302, a drain region 303, a channel region 304, an insulator dielectric 305, where the interface 306 of the insulator dielectric 305 not in contact with the substrate 301, or the dielectric region 307 forming the detection area, contains a large number of what are known as interface states. Ions attach themselves to these interface states according to the concentration of the parameter under analysis of the medium 308 to be characterized; these would be H+ ions if the field effect transistor 300 were designed as a pH-value sensor. In other words, this means that an interaction takes place between the medium 308 under investigation and the field effect transistor 300. The potential effect caused by the interaction acts in a deterministic way on the channel current made up of the charge carriers within the channel region 304, or rather on the density of the charge carriers present in the channel region 304 of the field effect transistor 300.

In particular in biosensor or bioelectronics technology, it is desirable to provide a large number of such field effect transistor sensors described above in a sensor array, in order to enable detection with precise spatial resolution and temporal resolution of one or more parameters to be detected of a given specimen, for example of a specimen containing cells 206 or of a gas specimen as medium 308.

One possible application of such sensor arrays can be found in the characterization of the neural activities of a multiplicity of mutually coupled biological cells. In such a sensor array, the sensors, i.e. the field effect transistors, are meant to be arranged in a matrix containing several thousand field effect transistors along each row and each column, each sensor having a mutual separation that is less than 5 $\mu$m*5 $\mu$m. The signal range of the electrical signal to be detected that is available in such an application can have values here of the order of magnitude of several microvolts ($\mu$V).

In addition, an array having a multiplicity of transistors and a multiplicity of sensor elements is known from [4], each sensor element being connected in series with a transistor. The transistors share a common source-follower resistor connected to the common series output of the transistors.

BRIEF SUMMARY OF THE INVENTION

In [5], a method for the manufacture of micro-and nano-structured carbon layers, carbon electrodes and chemical field effect transistors is known.

The invention is based on the problem of defining a sensor array, which, for a very high spatial resolution, up to a spatial resolution at which the field effect transistors are spaced down to 5 μm *5 μm and below, having a very large number of field effect transistors, from up to several thousand up to several million, can be used to detect bioelectric signals.

In addition, the invention is based on the problem of defining a method for detecting a condition of a transistor in a sensor array having up to several million field effect transistors arranged with a spatial resolution of down to 5 μm*5 μm and below, where the field effect transistors can be used to detect bioelectric signals.

The problem is solved by the sensor array and by the method for detecting a condition of a transistor in a sensor array having the features claimed in the independent claims.

A sensor array contains transistors (transistor elements) that are coupled together. The transistors themselves, preferably field effect transistors, are designed as sensors. In addition, a means of selection is provided that is used for selecting a transistor whose condition is to be detected. The sensor array is set up so that the selected transistor itself can be driven as a source follower, at least when selection has been made.

In a method for detecting a condition of a transistor in a sensor array that contains transistors coupled together, the transistors are used as sensors. This means that the condition of a transistor depends on a signal to be detected, which is detected by the transistor. The transistor is selected, and the condition of the selected transistor is detected. The selected transistor is driven as a source follower, at least when selection has been made.

By means of the invention, it is possible for the first time to produce a sensor array containing a large number of transistors, up to several million transistors, as a sensor array with a high spatial resolution and high temporal resolution.

In particular, by driving the selected transistor as a source follower, i.e. at an operating point at which the source voltage of the selected field effect transistor has an essentially linear dependence on the gate voltage applied to the field effect transistors, which represents the potential of the specimen under investigation, the array having this high level of spatial and temporal resolution becomes essentially noise-free and thus stably possible.

The sensor array is robust to interference effects and it is ensured that the bioelectric signals, for instance from the cell 206 or the medium 308, can be detected very precisely.

Preferred development of the invention arise from the dependent claims.

At least some of the transistors can be field effect transistors. According to an embodiment of the invention, at least some of the field effect transistors are MOS field effect transistors.

At least some of the MOS field effect transistors can be set up so that they can detect biological material.

According to a further embodiment of the invention, there is provision for at least some of the transistors to be ion-sensitive field effect transistors. In this way it is possible to use the sensor array in gas sensor technology or to find a pH value of solutions for instance.

The selected transistor can be driven as a source follower for example. The selected transistor can be driven at an operating point in inversion, at least when selection has been made. Alternatively, the selected transistor can be driven at an operating point in the sub-threshold region of the transistor, at least when selection has been made.

According to a further embodiment of the invention, there is provision to apply a voltage, equal to the operating voltage of the sensor array, in order to detect a condition of the selected transistor. This development makes it possible to implement the whole sensor array very compactly and easily, since the operating voltage can also be used to detect the condition of the selected transistor concerned.

The transistors can be arranged compactly in columns and in rows in the form of a matrix, and coupled together via column connections and row connections similar to the connecting structure of a matrix of a standard semiconductor memory.

According to a further embodiment of the invention, a current source is provided that can be coupled to the source contacts of the field effect transistors. A voltage source can also be provided that can be coupled to the drain contacts of the field effect transistors. The sensor array according to this embodiment is particularly suited to compensating for signal errors that may arise within the sensor array.

The means of selection may contain switches, by means of which a transistor can be selected.

In particular, in order to reduce possible parasitic effects, which can arise in the sensor array, particularly for reduced dimensions of the sensor array for a constant or growing number of field effect transistors, provision is made according to an embodiment of the invention to assign to each transistor a selection element, which can be used to couple the selected transistor conductively to the means of selection, and which can be used, when the transistor is not selected, to cut off the current flow through it electrically.

The selection element can be a diode or a transistor.

In addition, a buffer circuit, using an operational amplifier for instance, can be provided, which is coupled to the transistors, preferably to the row connections of the field effect transistors. Using the buffer circuit, the condition detected at the time is made available, via the row connections and the buffer element, at an output of the buffer circuit for further processing, where, for example, the signal representing the condition and made available at the output is of low impedance and capable of taking a load. Alternatively, within the scope of the invention, any electrical circuit that guarantees the functionality described above can be used as buffer circuit, i.e. that guarantees that an input signal present at the input of the buffer circuit is made available at low-impedance at the output of the buffer circuit.

Thus by means of the buffer circuit, the signals taken off at its output are prevented from having a loading effect on the sensor array.

It is preferred to make the signal present at the output of the buffer circuit available via column connections to the transistors of the sensor array, in order to provide at least some of the unselected transistors with a defined electrical potential equal to the potential present at the output of the buffer circuit.

Exemplary embodiments of the invention are depicted in the figures and explained in more detail below.

DETAILED DESCRIPTION OF THE INVENTION

Identical elements in the figures are labeled below with the same references.

Figure 1:
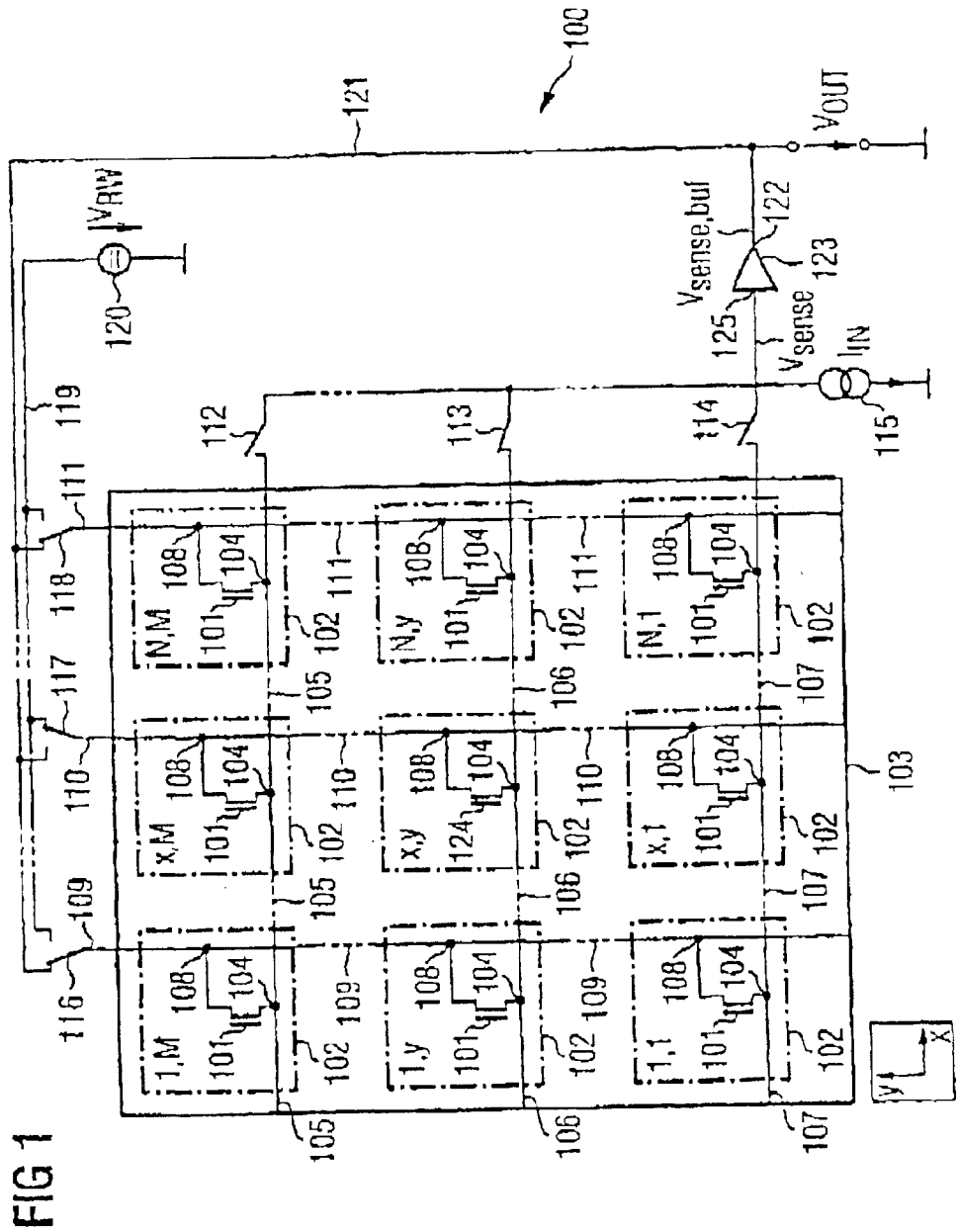
FIG. 1 shows a sensor array according to a first exemplary embodiment of the invention.

FIG. 1 shows a sensor array 100 according to a first exemplary embodiment of the invention.

The sensor array 100 contains MOS field effect transistors 101 designed as a sensor.

Figure 2:
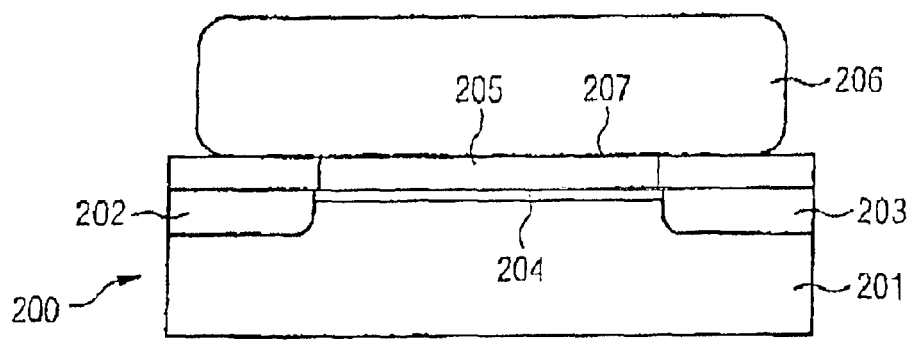
FIG. 2 shows a sketch of a field effect transistor with biological material.
Figure 3:
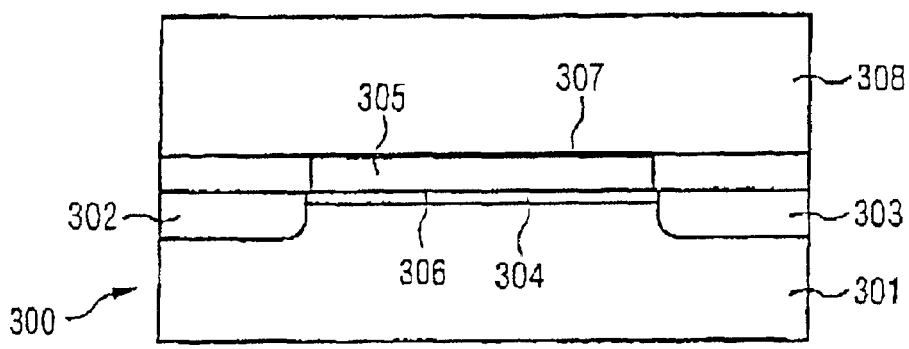
FIG. 3 shows a sketch of an ion-sensitive field effect transistor.

The field effect transistor depicted in FIG. 2 or in FIG. 3 may be used, for instance, as such a field effect transistor.

In addition, the field effect transistors described in [1] and [2] may alternatively be used as sensor in the sensor array 100.

Each field effect transistor 101 forms a sensor cell 102.

The sensor array 100 contains M * N sensor cells 102, the sensor cells 102, and hence the field effect transistors 101, being arranged in N columns and M rows in the form of a matrix 103. This means that the sensor array 100 contains N sensor cells 102 in each row. The sensor array 100 contains M rows, i.e. M sensor cells 102 in each column of the sensor array 100.

Figure 4:
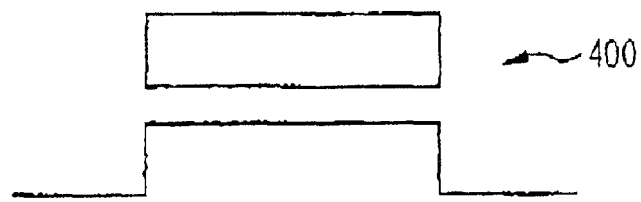
FIG. 4 shows a sketch of a symbol of a transistor designed as a sensor, which is used in the description of the exemplary embodiments.

FIG. 4 shows the symbol 400 for a field effect transistor 101 as used in the description below.

Each of the source contacts 104 of each field effect transistor 101 is coupled to a row connection (an electrical conductor) 105, 106, 107, so that each of the source contacts 104 of all the field effect transistors 101 in one row is coupled to a row connection 105, 106, 107.

The drain contacts 108 of all the field effect transistors 101 are coupled to the column connections 109, 110, 111, preferably electrical conductors, so that each of the drain contacts 108 of the field effect transistors 101 in one column is coupled to the corresponding column connection 109, 110, 111.

A row-selection switch 112, 113, 114 is connected to each row connection 105, 106, 107 respectively as means of selection. If the row-selection switch 112, 113, 114 in question is in the open position, then no current flows through the corresponding row connection 105, 106, 107.

If, however, the row-selection switch 112, 113, 114 in question is closed, then an injected current $I_{IN}$ provided by a current source 115 flows through the corresponding row connection 105, 106, 107.

In addition, a column-selection switch 116, 117, 118 is provided as means of selection for each column connection 109, 110, 111 respectively.

In a first switch position, which corresponds to selecting the relevant column connection 109, 110, 111, i.e. in the case that a field effect transistor 101, which is coupled to the column connection 109, 110, 111 selected at the time, in FIG. 1 the second column connection 110, is meant to be selected, the column connection 109, 110, 111 selected at the time is coupled to a first connecting line 119, which is coupled to a voltage source 120. The voltage source 120 supplies an operating voltage $V_{RW}$, which is used to select the relevant field effect transistor 101 or 124.

In the second switch position, the relevant column-selection switch 116, 117, 118 is connected to a second connecting line 121, via which the switch concerned is coupled to the output 122 of a buffer circuit 123.

The buffer circuit 123 may, as shown in the exemplary embodiments, be an operational amplifier for instance, whose non-inverting input can be coupled to the row connections 105, 106, 107, and whose inverting input is coupled to the output of the operational amplifier.

It must be noted in this context that a different electrical circuit, which makes an input signal present at its input available at low impedance at its output, can be used directly instead of the buffer circuit 123.

The electrical potential of the signal that acts on the channel region of the field effect transistor 101 concerned, i.e. the signal to be characterized by the field effect transistor as sensor, is referred to below by $V_{char}$.

By selecting the row-selection switches 112, 113, 114 and the column-selection switches 116, 117, 118, the injected current $I_{IN}$ is injected into the field effect transistor 124 of the selected row, in FIG. 1 the second row connection 106.

A buffered measurement signal $V_{sense,buf}$ present at the output 122 of the buffer circuit 123, which in terms of its value is equivalent to the measurement signal $V_{sense}$ amplified with a gain of 1, is fed to the sensor array 100 by means of the column-selection switches 116, 117, 118, specifically to the column connections 109, 111 of the field effect transistors 101 that have not been selected.

This arrangement ensures that all the field effect transistors 101 that are coupled to an unselected column connection 109, 111 are driven with a potential difference of zero volts between drain and source of the corresponding field effect transistor 101, and thus carry no current.

Hence this ensures that the injected current $I_{IN}$ flows without loss through the selected sensor transistor 124 at the position (x, y), where x refers to the column containing the selected field effect transistor, and y refers to the row containing the selected field effect transistor.

It must be noted in this context that the unselected row connections 105, 107 may be connected in theory to any potential within the specific operating-voltage limits set by the technology employed for the corresponding sensor array.

Alternatively, the relevant row-selection switches can simply be opened.

In addition, it is possible alternatively to couple all unselected row connections 105, 107 to the output 122 of the buffer circuit 123.

This coupling has advantages, particularly with regard to the access time to a field effect transistor 101 within the sensor array 100, since the potential of the row connection just selected in each case is, at the time of its selection, already lying close to the potential value that is being determined by the sensor just selected. Thus a smaller amount of electrical charge needs to flow until the new potential is set up.

Figure 5A:
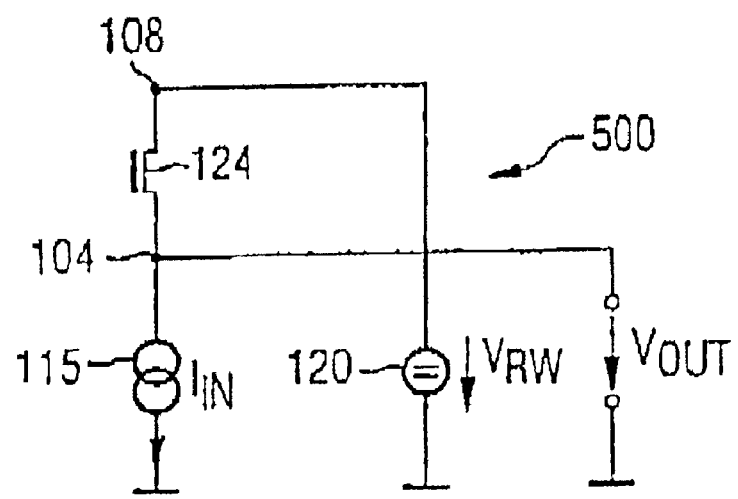
FIGS. 5a and 5b show electrical equivalent circuits of the sensor array shown in FIG. 1 without buffer circuit (FIG. 5a) and with buffer circuit (FIG. 5b).
Figure 5B:
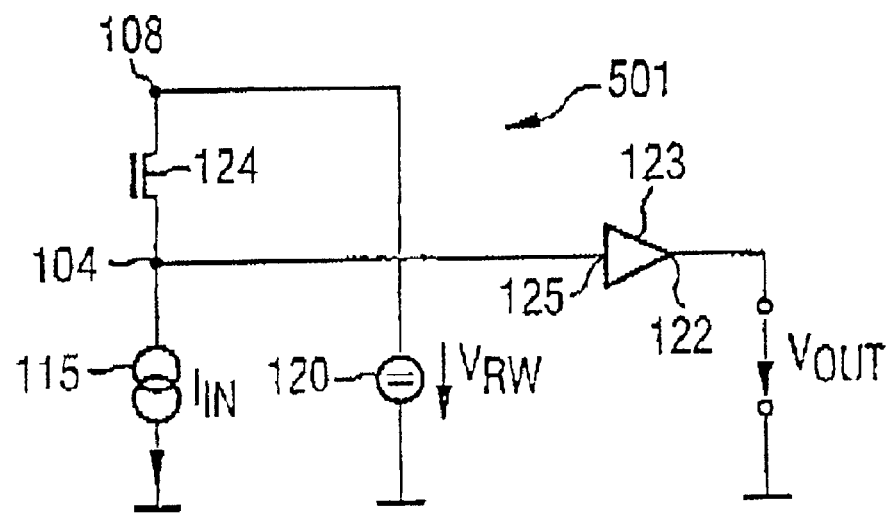

FIG. 5a and FIG. 5b show the electrical equivalent circuit for the selected field effect transistor 124 of the sensor array 100 depicted in FIG. 1, where FIG. 5a shows the electrical equivalent circuit 500 without buffer circuit 123, and FIG. 5b shows the electrical equivalent circuit 501 with buffer circuit 123, which makes no difference, however, as regards the value of the output signal $V_{OUT}$ of this circuit.

The value of the source voltage $V_S$ of the selected field effect transistor 124, i.e. of the selected sensor transistor, whose value is identical to the potential $V_{sense}$ present at the input to the buffer circuit 123, is a function of the potential $V_{char}$ acting on the channel region of the selected field effect transistor 124, of the current through the selected field effect transistor 124, which is equal to the injected current $I_{IN}$, and of the drain voltage at the selected field effect transistor 124, this being the operating voltage $V_{RW}$ in FIG. 1.

The injected current $I_{IN}$ is selected such that the selected transistor 124 adopts an operating point so that the selected field effect transistor 124 is driven as a source follower.

This is possible by the injected current $I_{IN}$ being selected so that the selected field effect transistor 124 adopts an operating point in inversion, i.e. the following applies:

$$V_{char} - V_s > V_{th}, \quad (1)$$

where $V_{th}$ refers to the threshold voltage of the field effect transistor 124, and by the drain voltage being selected to be greater than the difference $$V_{char} - (V_{th} + V_s), \quad (2)$$

which equals what is known as the effective gate voltage of the selected field effect transistor 124.

In this way, an operating point of the field effect transistor 124 is set up in the saturation region, and the field effect transistor is driven as a source follower, as required.

This situation exploits the fact that under the cited conditions, the transistor current only exhibits a weak dependence on the drain voltage of the selected field effect transistor, and is mainly determined by the effective gate voltage.

Since the current is preset, however, and the voltage $V_{char}$ is the variable to be characterized, i.e. the signal to be detected, this clearly results in an essentially linear mapping of the voltage $V_{char}$ onto the source voltage $V_S$ of the selected field effect transistor.

Since, as is apparent from FIG. 1, the following holds:

$$V_{sense} = V_s, \quad (3)$$

then at the selected second row connection 106 there is
a detected signal $V_{char}$ that is changed by a constant amount. Changes $\Delta V_{char}$ in the electrical signal to be detected $V_{char}$ hence lead to changes $\Delta V_{sense}$ at the selected row connection 106, where the following is true to a good approximation:

$$\Delta V_{sense} = \Delta V_{char}. \quad (4)$$

The positive operating voltage $V_{DD}$ used to drive the sensor array 100 is preferably chosen as the value for the voltage $V_{RW}$.

Alternatively, the selected field effect transistor 124 concerned can also be driven at an operating point in what is known as the sub-threshold region, i.e. such that the following is true:

$$V_{char} - V_S < V_{th}. \quad (5)$$

Such an operating point can be set if a very small current $I_{IN}$ is injected.

Also in this case, the change in the source voltage of the selected field effect transistor is approximately linearly dependent on the change in the electrical signal $V_{char}$ acting on the selected field effect transistor 124.

The buffered measurement signal $V_{sense,buf}$ made available at the output 122 of the buffer circuit 123 is used as output signal of the sensor array 100, which can be employed in further signal-processing circuit components not shown, or alternatively evaluated directly.

The buffered measurement signal $V_{sense,buf}$ made available at the output 122 of the buffer circuit 123 is of low impedance and therefore capable of taking a load, i.e. signal processing can take place without any fears of the sensor array 100 being loaded by the signal processing.

Provided the measurement signal is taken off with sufficiently high impedance, for example using an amplifier whose inputs are formed by the gates of MOS field effect transistors, the measurement signal $V_{sense}$ can also be used directly as output signal.

Figure 6:
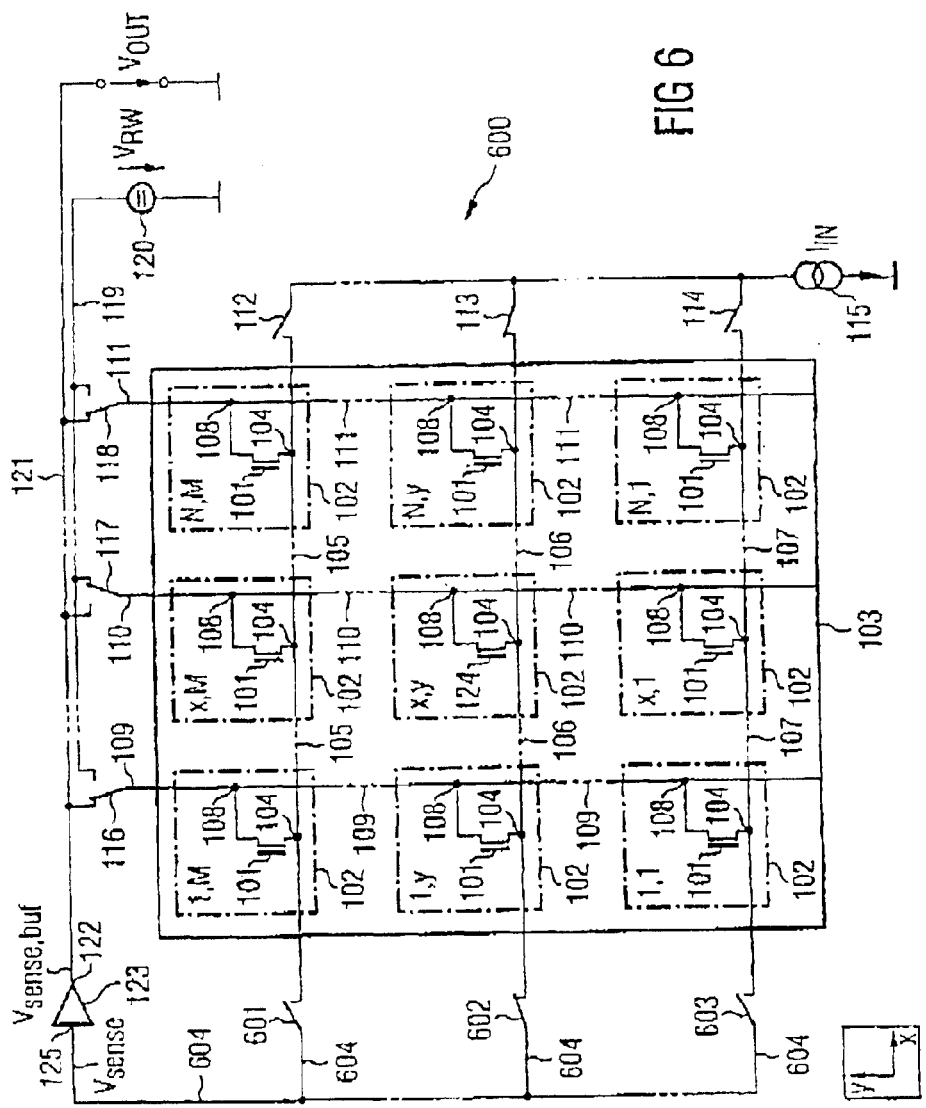
FIG. 6 shows a sensor array according to a second exemplary embodiment of the invention.

In a sensor array 600 according to a second exemplary embodiment, which is shown in FIG. 6, extra row-selection switches 601, 602, 603 are provided in addition to the row-selection switches 112, 113, 114, which are arranged on the opposite side of the sensor array 600 from the row-selection switches 112, 113, 114.

According to the sensor array 600 shown in FIG. 6, the injected current $I_{IN}$ is fed from the current source 115 via the row-selection switches 112, 113, 114 to the selected row connection 106. The selected voltage signal $V_{sense}$ is taken off via the extra row-selection switches 601, 602, 603 of the selected row connection 106, and fed via connecting lines 604 to the input of the buffer circuit 123 as measurement signal $V_{sense}$, a buffered output signal $V_{sense,buf}$ thereby being generated from the buffer circuit 123.

The other elements of the sensor array 600 according to the second exemplary embodiment correspond to the sensor array 100 according to the first exemplary embodiment.

Figure 7:
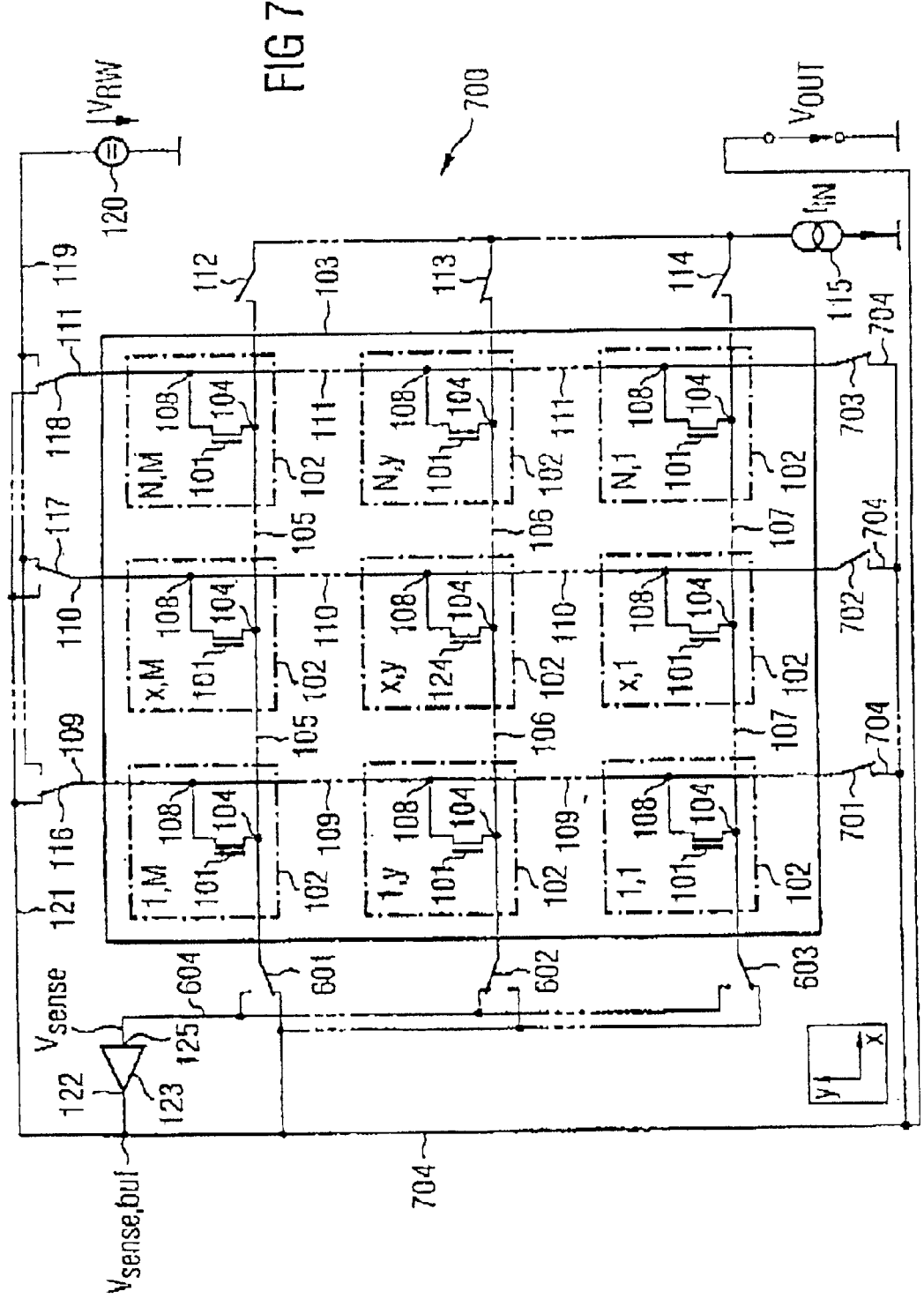
FIG. 7 shows a sensor array according to a third exemplary embodiment of the invention.

FIG. 7 shows a sensor array 700 according to a third exemplary embodiment of the invention.

According to the third exemplary embodiment, extra column-selection switches 701, 702, 703 are provided compared with the sensor array 600 according to the second exemplary embodiment.

In addition, the buffered measurement signal $V_{sense,buf}$ at the output 122 of the buffer circuit 123 is fed back to the extra row-selection switches 601, 602, 603 via feedback connections 704 in such a way that the unselected row connections 105, 107 are coupled to the buffered measurement signal $V_{sense,buf}$ because of the corresponding switch position of the row-selection switches 601, 603, in which they are coupled to the corresponding feedback connection 704.

Figure 8:
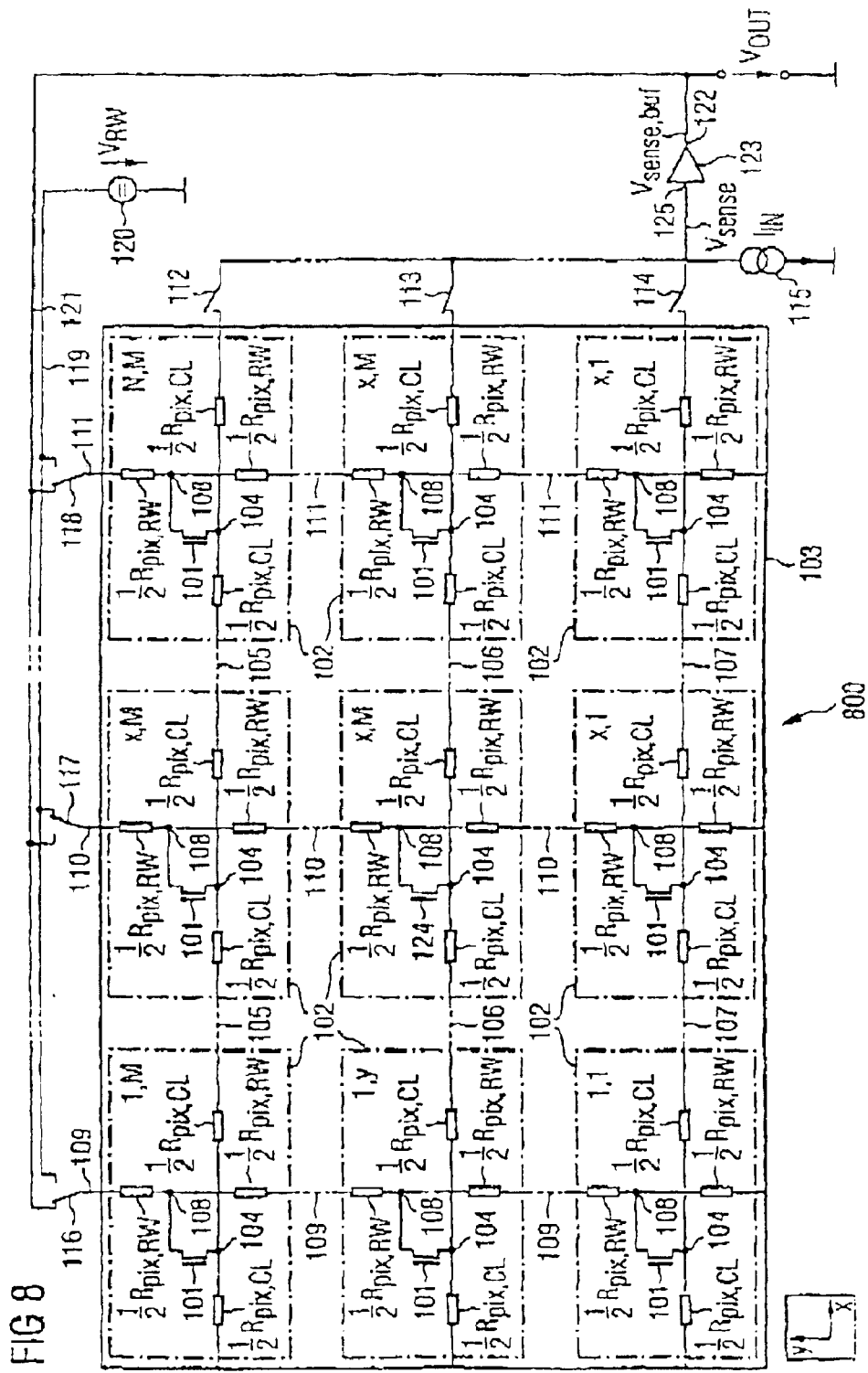
FIG. 8 shows the sensor array as shown in FIG. 4, taking into account in addition parasitic resistances in the connecting lines between the individual field effect transistors.

FIG. 8 shows a sensor array 800 in which parasitic effects are taken into account.

This sensor array 800 shows parasitic resistances $R_{pix,RW}$, $R_{pix,CL}$, which arise for each sensor cell 102 as a result of the row connections 104, 105, 106 and the column connections 109, 110, 111.

For each sensor cell 102, a given section of the corresponding column connection 109, 110, 111 or of the corresponding row connection 104, 105, 106 is taken into account by the parasitic resistance $$R_{pix,RW}\left(=2\cdot\frac{1}{2}\cdot R_{pix,RW}\right) \text{ or } R_{pix,CL}\left(=2\cdot\frac{1}{2}\cdot R_{pix,CL}\right).$$

The parasitic resistances $R_{pix,CL}$ and $R_{pix,RW}$ cause voltage drops on the row connections 105, 106, 107 and column connections 109, 110, 111 respectively, so that a relatively complex profile of the node potentials of all the nodes in the sensor array 800 is obtained within the sensor array 800 overall.

If the sensor array 800 is designed so that the dimensions, i.e. the distances between the individual sensor cells 102, of the sensor array 800 are further reduced for a constant or increasing number of field effect transistors contained in the sensor array, then these parasitic resistances $R_{pix,CL}$ and $R_{pix,RW}$ should be taken into account, first because it is no longer absolutely guaranteed in this case that the injected current $I_{IN}$ flows completely through the selected field effect transistor 124. This is the case here, since drain-source voltages not equal to the value 0 arise across the unselected transistors 101 within a selected row, i.e. within a row that also contains the selected transistor 124, as a result of the previously described complex voltage drop across the whole array, so that these transistors also carry current.

Secondly, the voltage drop on the row connection 105, 106, 107 or column connection 109, 110, 111 between the current source 115 and the source 104 of the selected field effect transistor 124, means that the measurement voltage $V_{sense}$ is no longer identical to the source voltage of the selected field effect transistor 124. The difference between the measurement voltage $V_{sense}$ and the source voltage $V_g$, and the difference between the injected current $I_{IN}$ and the current actually flowing through the selected field effect transistor 124, are also dependent on the position of the selected field effect transistor 124 within the matrix 103 of the sensor array 800.

Figure 9:
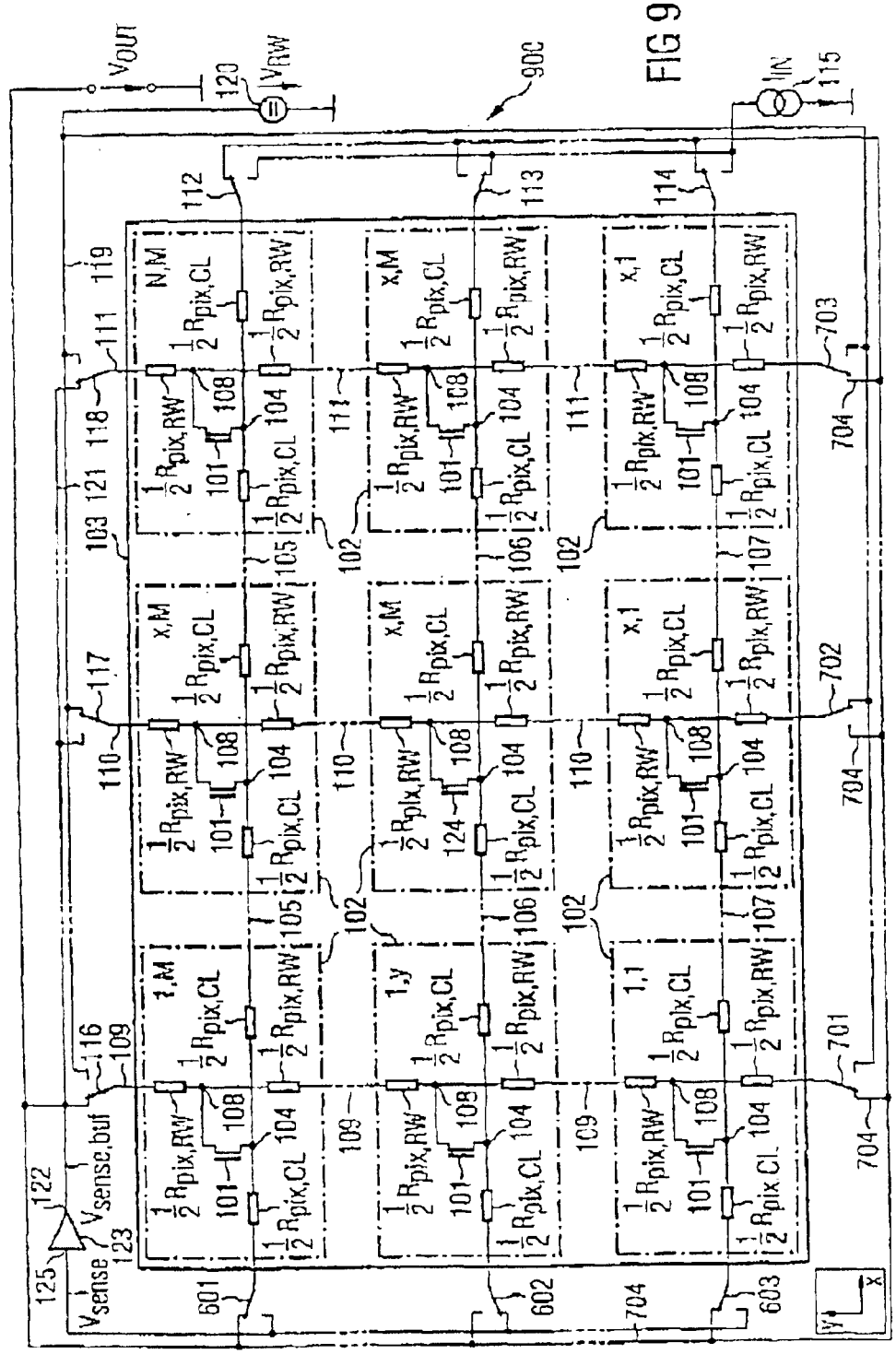
FIG. 9 shows a sensor array according to a fourth exemplary embodiment of the invention.

FIG. 9 shows a sensor array 900 which is used to minimize the problems set out above when dimensions of the sensor array 800 are further reduced for a constant or increasing number of field effect transistors contained in the sensor array, i.e. to provide optimum compensation for the measurement errors resulting from the parasitic resistances $R_{pix,CL}$ and $R_{pix,RW}$.

Compensation is made possible in particular by the fact that the injection of the injected current $I_{IN}$ by means of the current source 115 is performed in each case on the opposite side of the sensor array 900 from the detection of the measurement signal $V_{sense}$, and that the buffered measurement voltage $V_{sense,buf}$ at the output 122 of the buffer circuit 123 is applied not only to the column connections 116, 117, 118, but also on both sides of the array to the unselected row connections 105, 107. In addition, the column potentials are applied to both sides of the column connections 116, 117, 118 of the sensor array 900.

This sensor array 900 has the effect that that section of the row connections 105, 106, 107 that couples the source of the selected field effect transistor 124 to the input 125 of the buffer circuit 123, i.e. to the buffer circuit 123, carries approximately no current. Thus there is also approximately no voltage drop on this section of the row connection, and the signal present at the source of the selected field effect transistor can be read from the sensor array 900 with almost no alteration.

In order for it also to be possible to operate without measurement errors a sensor array 900 having very many elements or having small geometrical dimensions per sensor cell 102, and in order to improve the sensor array 900, particularly with regard to driving the field effect transistors with relatively large currents in order to reduce the access time to the selected field effect transistor 124, extra selection elements are provided in addition to the field effect transistors 101, in the sensor cell 102 within the sensor array 900, in order to decouple the corresponding field effect transistors 101, by means of which selection elements, using control signals, a targeted selection of the desired field effect transistor is possible without any alteration of the signal to be characterized, detected by the selected field effect transistor.

Such sensor arrays 900 having extra selection elements are described below.

These exemplary embodiments share the common feature that the injection of the injected current $I_{IN}$ is performed in each case on the opposite side of the sensor array from the detection of the measurement signal $V_{sense}$, and meet the following two fundamental conditions:

The injected current $I_{IN}$ flows completely via the selected sensor transistor 124, i.e. via the selected field effect transistor 124 that is designed as sensor.

A voltage drop arises only across that section of the row connections connected to the source of the selected sensor transistor 124 and running in the x-direction that lies between the source of the selected sensor transistor and the current source 115. The section of this row connection that is arranged between source of the selected sensor transistor and the signal pick-up point of the measurement signal $V_{sense}$, carries no current, so that no voltage drop arises on this section of the row connection, and the signal present at the source of the selected sensor transistor 124 can be read from the sensor array without alteration.

The following nomenclature is also used in the description below. The sensor array contains N columns 109, 110, 111, where $1 \leq x \leq N$, and M rows 105, 106, 107, where $1 \leq y \leq M$, the selected sensor element 124 being located at the position (x, y) within the sensor array.

Compliance with these two conditions cited above is ensured, in particular, by the fact that only the selection element at the column position of the selected sensor transistor 124, i.e. the selection element in the sensor cell of the selected field effect transistor, is in the open state, or is driven in this way, whilst all other selection elements to be assigned to the same row at the positions (1, y) . . . , (x−1, y), (x+1, y), . . . , (N, y) are in the blocked state, or are driven in this way.

Figure 10:
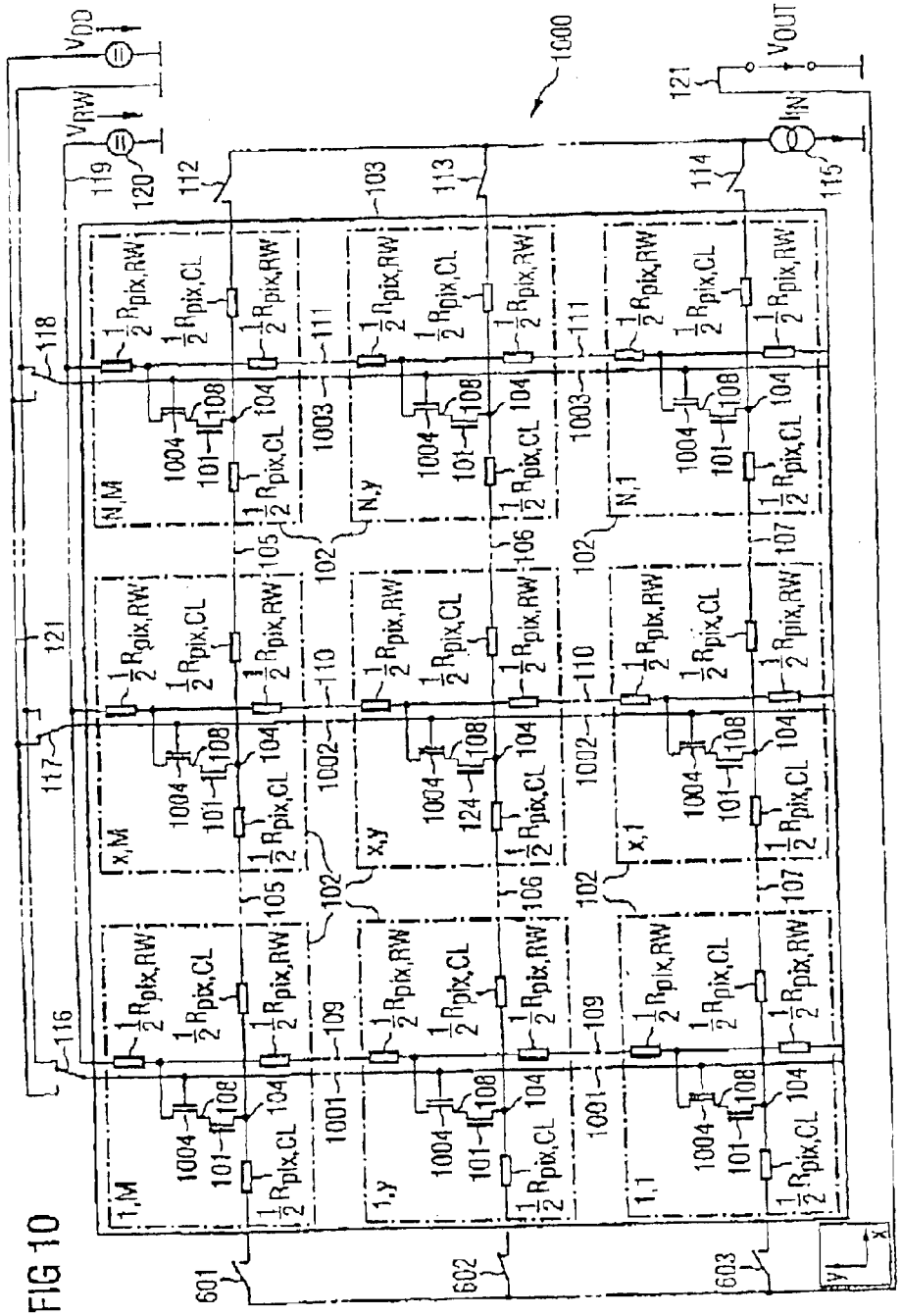
FIG. 10 shows a sensor array according to a fifth exemplary embodiment of the invention, in which each field effect transistor is assigned a selection element.

FIG. 10 shows a sensor array 1000 according to a fifth exemplary embodiment, which complies with the conditions cited above. The parasitic resistances $R_{pix,CL}$ and $R_{pix,RW}$ are drawn in the sensor cells 102. The parasitic resistances also arising in the extra selection lines 1001, 1002, 1003 are not shown, as they do not cause any measurement errors during operation of the sensor array 1000.

Each sensor cell 102 contains two active elements, namely the actual sensor transistor 101 and a selection transistor 1004 in each case. The selection transistors 1004 are driven via the extra selection connections 1001, 1002, 1003 running in the y-direction.

The positive operating voltage $V_{DD}$ is, for example, applied to the extra selection line 1002 of the selected sensor transistor 124, the column-selection switches 116, 118 being coupled to the negative operating voltage at the positions (x, 1), . . . (x, M).

A low level (i.e. a negative operating voltage $V_{SS}$) is applied to all the other control lines 1001, 1002, 1003, so that all the selection transistors 1004 at these positions are in the non-conducting state.

Regarding the choice of the injected current $I_{IN}$ and the voltage $V_{RW}$, these parameters are chosen so that the selected sensor transistor 124 is driven at a suitable operating point in the saturation region or in the sub-threshold region, so that source-follower operation is possible.

It must be taken into account, that the drain voltage of the sensor transistor 101 of the corresponding sensor cell 102 is not determined solely by the value of the operating voltage $V_{RW}$ and the voltage drops along the line running in the y-direction, i.e. column connection 109, 110, 111, that is connected to the selection transistor 1004 of the selected sensor transistor 124, but also by the voltage falling across the selection element itself through which the current is flowing.

Once again, the positive operating voltage $V_{DD}$ can be selected for the voltage $V_{RW}$.

According to this exemplary embodiment, the unselected row connections 105, 107 may also be connected in theory to any potential or connected to a potential provided by the sensor arrays 900, by the corresponding row-selection switches 112, 114 simply being left in the open state, as depicted in FIG. 10.

Alternatively, the unselected row connections 105, 107 can be set to the potential $V_{RW}$. In this case the selection transistors 1004 and the sensor elements, i.e. the sensor transistors 101 at the positions (x, 1), . . . (x, y−1), (x, y+1), . . . (x, M), carry no current, and the voltage drops are minimized along the column connections 109, 110, 111 that couple the selection transistor 1004 of the selected sensor transistor 124 to the operating voltage $V_{RW}$, since this column connection need not take, in addition to the current flowing through the selected sensor transistor 124, any further currents flowing through unselected sensor transistors of the same column.

Alternatively, all unselected row connections 105, 107 can be coupled to the buffered measurement signal $V_{sense,buf}$ provided via a buffer circuit.

This array can have advantages when changing rows of the sensor position read out, or for the access time, since the potential of a row connection just selected is already lying close to the value that is being determined by the sensor just selected, and thus less electrical charge needs to flow until the new potential is set up.

In this context it should be noted in particular that for this version the buffer circuit 123 is not absolutely necessary.

Figure 11:
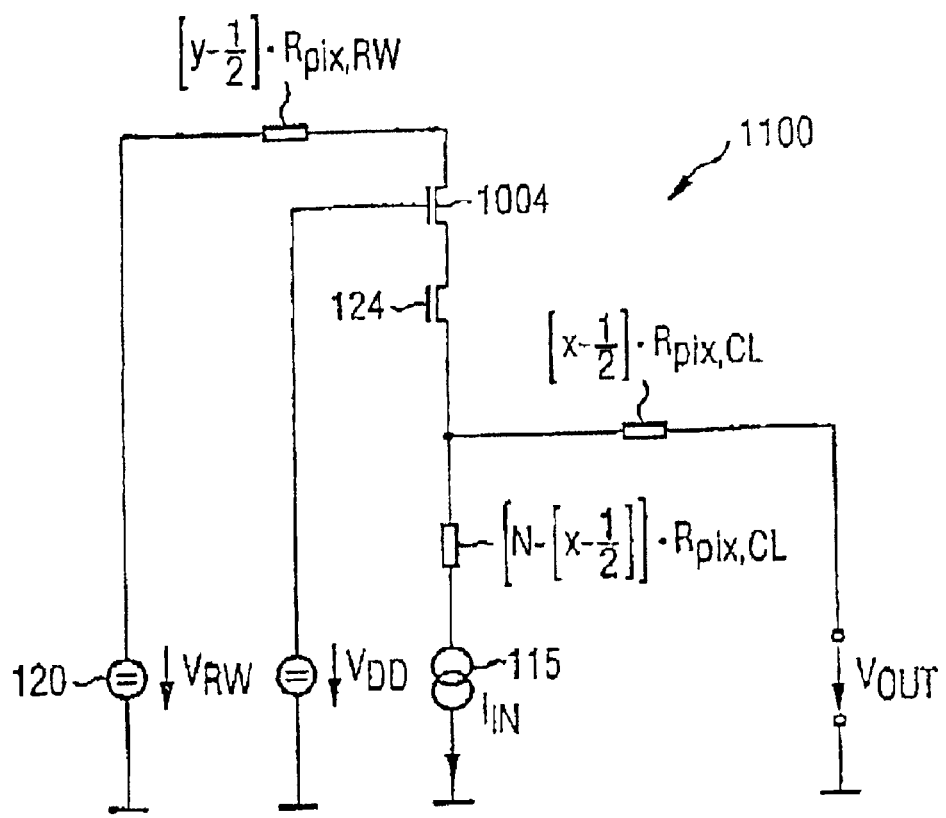
FIG. 11 shows the electrical equivalent circuit of the sensor array shown in FIG. 10.

FIG. 11 shows the electrical equivalent circuit 1100 of the sensor array 1000 shown in FIG. 10.

FIG. 11 also shows the values for the total parasitic resistances derived from $R_{pix,RW}$ and $R_{pix,CL}$ in the electrical equivalent circuit 1100 for a sensor cell 102 at the position (x, y).

As is apparent from FIG. 11, the selected sensor transistor 124 is again driven as source follower, and the output voltage $V_{out}$ provides the unaltered measurement result, since no current is carried on that section of the row connections connected to the source 104 of the selected sensor transistor 124 and running in the x-direction that leads to the measurement-signal pick-up point.

As is apparent from FIG. 10, in FIG. 10, the voltage $V_{RW}$ is applied in parallel to all lines connected to the selection transistors 1003, i.e. to the extra selection connections $RW_{d,1}, \ldots, RW_{d,N}$, but only on one side of the sensor array 1000. It can be advantageous to apply the voltage $V_{RW}$ to these lines on both sides, because in this case the total effective parasitic resistance in the y-direction $R_{tot,RW}$ $$R_{tot,RW} = \frac{1}{2} \cdot R_{pix,RW} + \sum_{i=1}^{y-1} R_{pix,RW} = \left(y - \frac{1}{2}\right) R_{pix,RW} \quad (6)$$

is reduced in the equivalent circuit 1100 from FIG. 11 to $$R_{tot,RW} = \frac{\left(y - \frac{1}{2}\right) \cdot \left[M - \left(y - \frac{1}{2}\right)\right]}{\left(y - \frac{1}{2}\right) + \left[M - \left(y - \frac{1}{2}\right)\right]} \cdot R_{pix,RW} = \quad (7)$$

$$= \left(y - \frac{1}{2}\right)\left[1 - \frac{y - \frac{1}{2}}{M}\right] \cdot R_{pix,RW}.$$

The value in equation (7) is obtained from the parallel connection of the line section lying above and below the selected sensor transistor 124.

In the sensor array 1000 shown in FIG. 10, there are twice as many column connections running in the y-direction compared with the sensor arrays shown in FIG. 1, FIG. 6, FIG. 7, FIG. 8 and FIG. 9. In order to improve this possibly unfavorable arrangement, and in order to reduce the lines overhead compared with the sensor arrays shown in FIG. 1, FIG. 6, FIG. 7, FIG. 8 and FIG. 9 to a factor of 1.5, the sensor array 1000 from FIG. 10 is modified as shown in FIG. 12, resulting in a sensor array 1200 according to a sixth exemplary embodiment.

Figure 12:
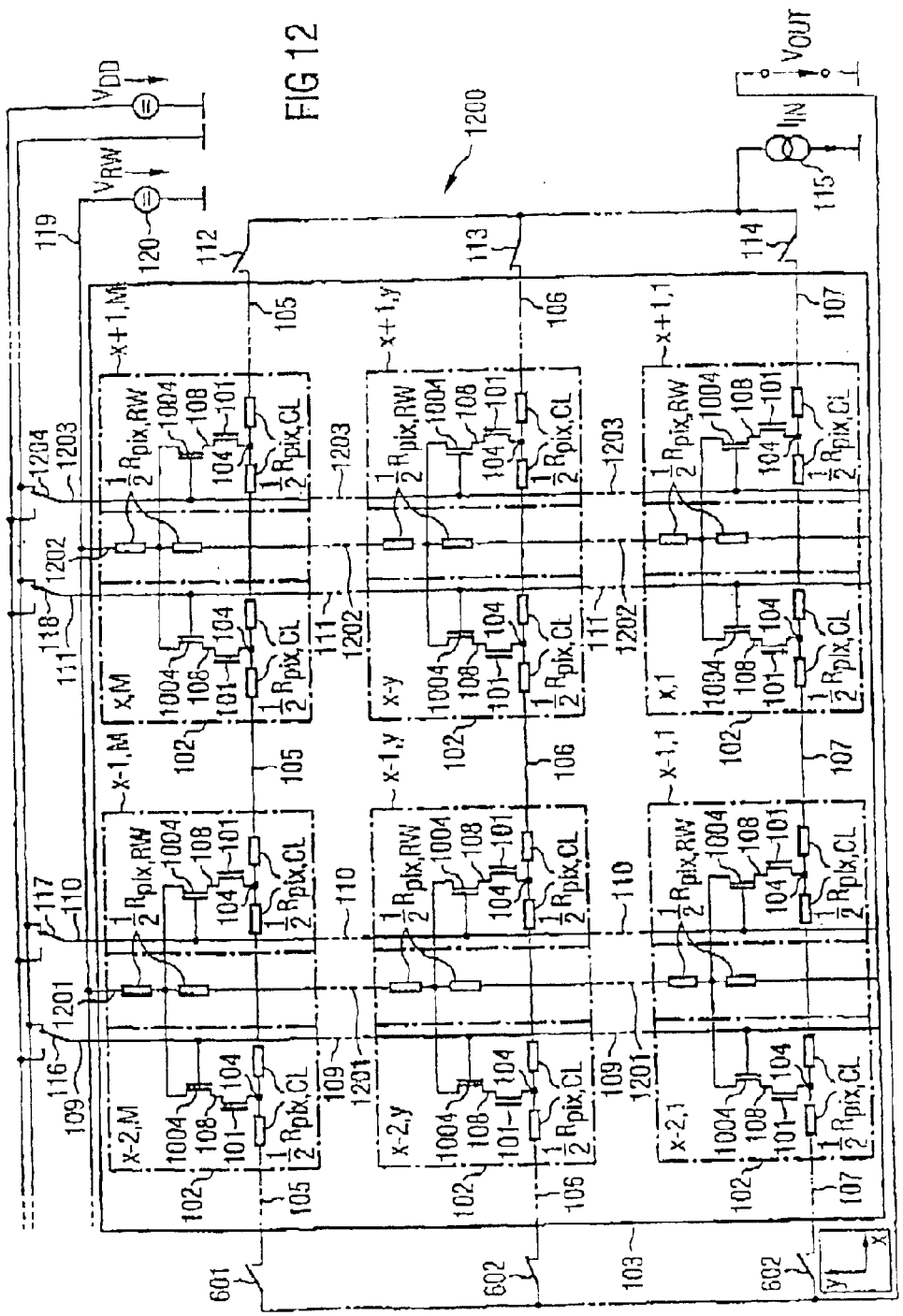
FIG. 12 shows a sensor array according to a sixth exemplary embodiment of the invention.

In the sensor array 1200 shown in FIG. 12, each pair of sensor cells 102 adjacent in the x-direction shares one selection line 1201, 1202 running in the y-direction. The column connections 109, 110, 111, 1203, however, continue to be taken individually to each column. In addition, an additional column-selection switch 1204 is also shown in FIG. 12.

In a further embodiment it is directly possible that more than two sensor cells 102 adjacent in the x-direction also share a supply line running in the y-direction.

Figure 13:
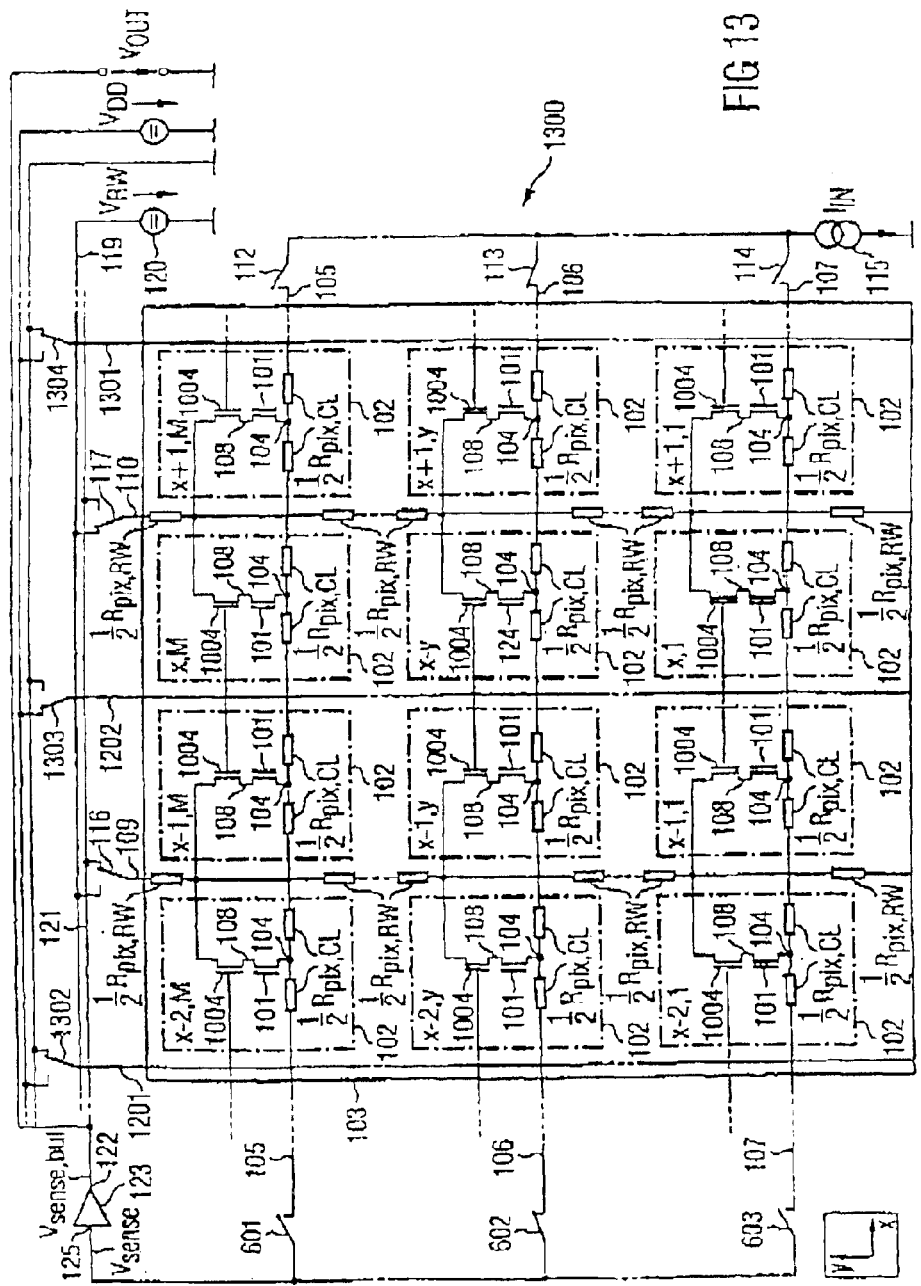
FIG. 13 shows a sensor array according to a seventh exemplary embodiment of the invention.

FIG. 13 shows a sensor array 1300 according to a seventh exemplary embodiment of the invention, in which all lines running in the y-direction, i.e. both the column connections 109, 110, 111 and selection lines 1201, 1202, 1301 are used with extra switches 1302, 1303, 1304 for selecting the sensor cell.

In this way, the overhead in additionally required column connections can be avoided completely. All column connections leading to the drain nodes or gate nodes of the selection transistors are coupled in each row to the drains or the gates respectively of each pair of adjacent selection transistors 1003.

Only the lines on the left and right edge of the sensor array 1300, which may be both drain supply lines and two gate lines or else one drain supply line and one gate line each, are coupled in each row to just one drain or gate of a selection transistor 1003.

In this way, the exact value for the factor specifying the overhead is equal to $$\frac{(M+1)}{M},$$

which is very close to 1 for large values of M.

The selection of a sensor cell 102 at the position y is made by the gate-selection line coupled to the corresponding selection transistor 1003 being taken to high level, i.e. to the positive operating voltage $V_{DD}$, whilst a low level, i.e. the negative operating voltage $V_{SS}$, is applied to all other gate lines to the left and right of this, so that all the selection transistors at these positions are in the non-conducting state.

In addition, the drain-selection line coupled to the corresponding selection transistor 1003 must be taken to operating voltage $V_{DD}$, and the other drain-selection lines are short-circuited to the output of the buffer amplifier or coupled to the ground potential.

Figure 14:
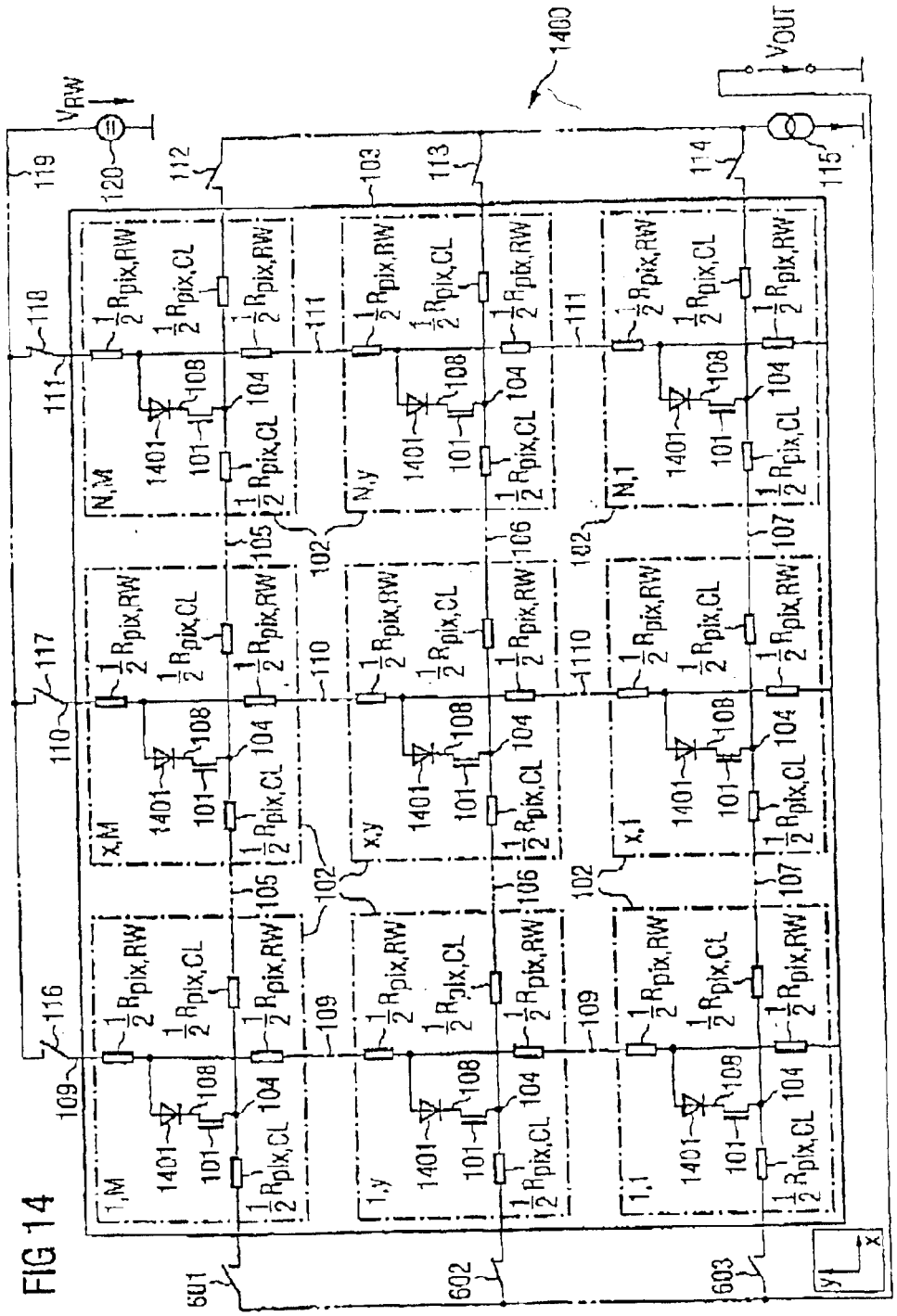
FIG. 14 shows a sensor array according to an eighth exemplary embodiment of the invention.

FIG. 14 shows a sensor array 1400 according to an eighth exemplary embodiment, in which a diode 1401 is provided for each sensor cell 102 as selection element. Unlike the sensor arrays 1000 and 1200, which are shown in FIG. 10 and FIG. 12, this sensor array 1400 requires exactly the same number of supply lines in the x- and y-direction as the sensor arrays shown in FIG. 1, FIG. 6, FIG. 7, FIG. 8 and FIG. 9.

The voltage $V_{RW}$ is again applied to the selected column connection; either a sufficiently low voltage, for instance the ground potential, can be applied to the unselected column connections, so that the diodes 1401 in these columns are reverse biased, or alternatively no connection may be made to a potential provided by the sensor array 1400, simply by leaving the corresponding column-selection switches in the open state.

This version is based on the principle that between the selected column connection and the selected row connection of the selected sensor transistor 124, no additional current path is created in which not at least one diode 1401 is in reverse bias.

The diodes 1401 and thus the assigned sensor transistors 101 in the unselected columns, i.e. in the unselected column connections, carry no current.

With regard to the choice of the potentials of the unselected row connections, or rather their drive potentials, the same applies as described in connection with FIG. 10.

Figure 15:
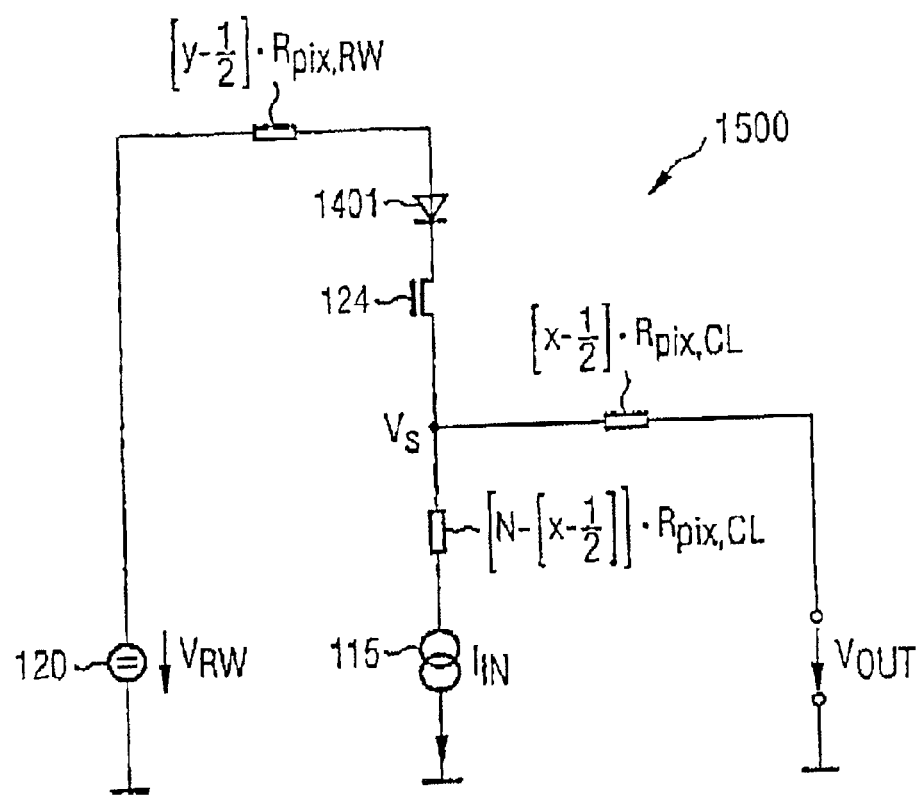
FIG. 15 shows an electrical equivalent circuit of the sensor array shown in FIG. 14.

FIG. 15 shows the electrical equivalent circuit 1500 belonging to the sensor array 1400 from FIG. 14.

Here the potentials can again also be fed to both sides of the supply lines running in the y-direction, which leads to the same results as have already been described above in connection with the sensor array 1000 from FIG. 10.

The diode 1401 of a sensor cell 102 in FIG. 14 and FIG. 15 can be implemented, for instance, by a pn-junction.

A MOS field effect transistor connected as a diode 1601, i.e. a MOS field effect transistor in which the drain and gate are connected together, can also be used, however.

Figure 16:
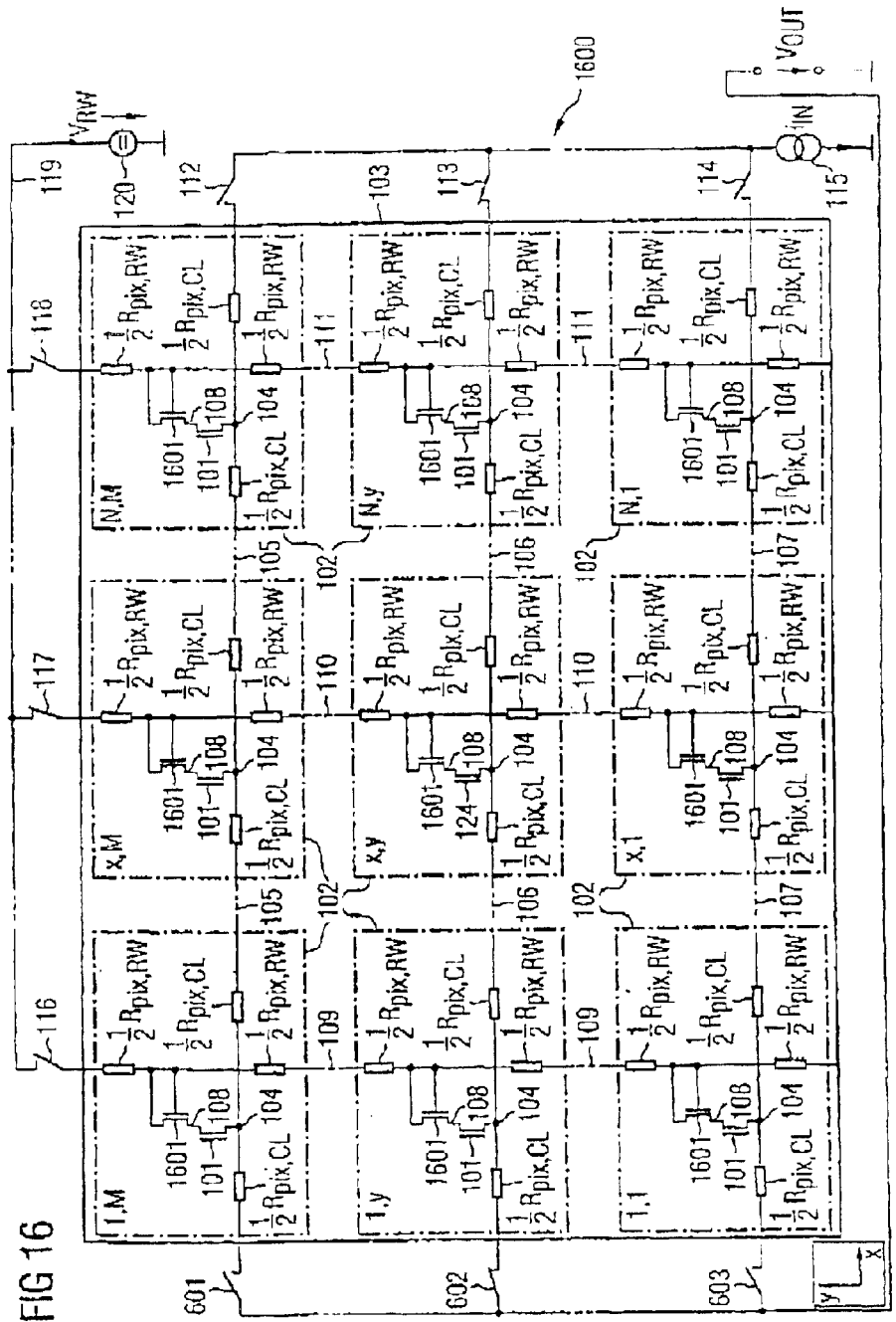
FIG. 16 shows a sensor array according to a ninth exemplary embodiment of the invention.
Figure 17:
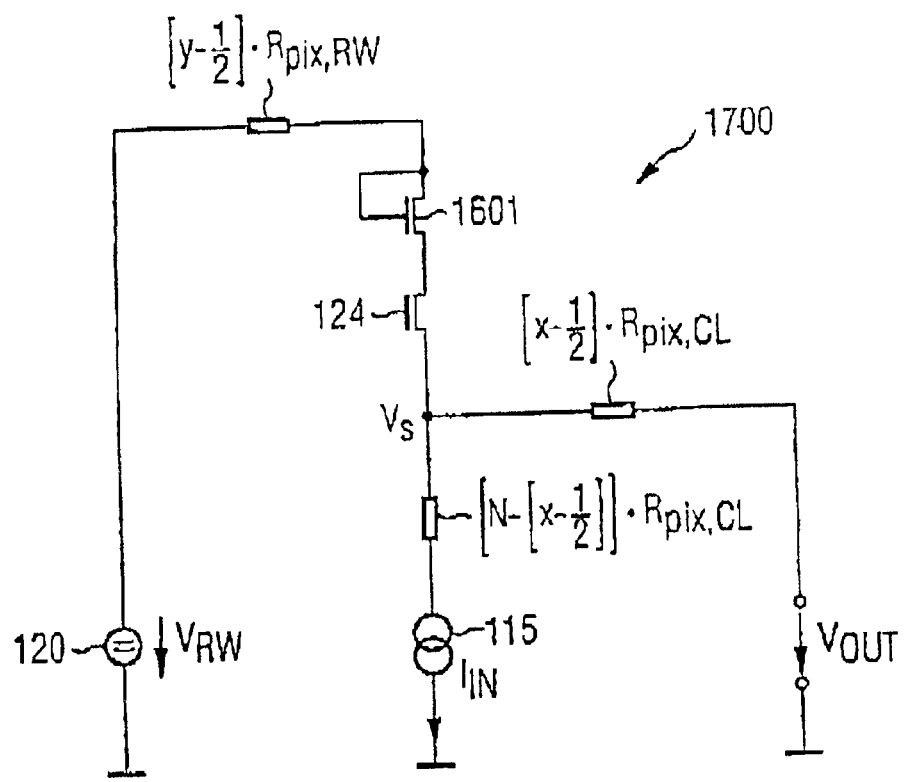
FIG. 17 shows an electrical equivalent circuit of the sensor array from FIG. 16.

In this case this yields the sensor array 1600 shown in FIG. 16 instead of the sensor array 1400 shown in FIG. 14, and the electrical equivalent circuit 1700 depicted in FIG. 17 instead of the electrical equivalent circuit depicted in FIG. 15.

The following publications are cited in this document:

[1] W. J. Parak et al, The field-effect-addressable potentiometric sensor/stimulator (FAPS) —a new concept for a surface potential sensor and stimulator with spatial resolution, Sensors and Actuators B, Chemical, Elsevier Science, pp. 497–504, 1999

[2] R. Weis and P. Fromherz, Frequency dependent signal transfer in neuron transistors, Physical Review B, p. 877 ff, 1997

[3] W. Baumann et al, Microelectronic sensor system for microphysiological application on living cells, Sensors and Actuators, p. 77 ff, 1999

[4] DE 35 13 617 C2

[5] DE 198 56 295 A1

What is claimed is:

1. A sensor array having transistors that are coupled together, the transistors being designed as sensors, the sensor array having a means of selection for selecting a transistor as a selected transistor whose condition is to be detected, the sensor array being set up so that the selected transistor is driven as a source follower, at least when selection has been made, and at least some of the transistors being MOS field effect transistors that are set up so that the at least some of the transistors are capable of detecting biological material.

2. The sensor array as claimed in claim 1, in which at least some of the transistors are ion-sensitive field effect transistors.

3. The sensor array as claimed in claim 1 in which the selected transistor is driven at an operating point in inversion, at least when selection has been made.

4. The sensor array as claimed in claim 1 in which the selected transistor is driven at an operating point in a subthreshold region, at least when selection has been made.

5. The sensor array as claimed in claim 1 in which the means of selection is set up so that, in order to detect a condition of the selected transistor, a voltage is applied that is equal to an operating voltage of the sensor array.

6. The sensor array as claimed in claim 1 in which the transistors are arranged in columns and in rows, and are coupled together via column connections and row connections.

7. The sensor array as claimed in claim 1 in which a current source is provided that is coupled to the source contacts of the field effect transistors.

8. The sensor array as claimed in claim 1 in which a voltage source is provided that is coupled to the drain contacts of the field effect transistors.

9. The sensor array as claimed in claim 1 in which the means of selection contain switches adapted for selecting a transistor.

10. The sensor array as claimed in claim 1 in which a selection element is provided for each transistor, which is used to couple the selected transistor conductively to the means of selection, and which is used to cut off a current flow through at least some of unselected transistors.

11. The sensor array as claimed in claim 10 in which the selection element is a diode or a transistor.

12. The sensor array as claimed in claim 1 in which a buffer circuit is provided, which is coupled to the transistors, where the selected transistor's condition being detected is buffered using the buffer circuit such that an input signal present at an input of the buffer circuit is made available at an output of the buffer circuit at low impedance.

13. The sensor array as claimed in claim 1 in which at least some of unselected transistors are coupled to one more defined electrical potentials.

14. The sensor array as claimed in claim 13 in which one of the one or more defined potentials is the signal made available at the output of the buffer circuit.

15. A method for detecting a condition of a transistor in a sensor array that contains transistors coupled together, the method comprising:

using the transistors as sensors in such a manner that the condition of a transistor depends on a signal to be detected, which is detected by the transistor, where at least some of the transistors are MOS field effect transistors that are set up so that the at least some of the transistors are capable of detecting biological material;

selecting one of the transistors as a selected transistor;

detecting the condition of the selected transistor;

driving selected transistors as a source follower, at least when selection has been made.

* * * * *

UNITED STATES PATENT AND TRADEMARK OFFICE
CERTIFICATE OF CORRECTION

PATENT NO. : 6,856,161 B2 Page 1 of 1
APPLICATION NO. : 10/239438
DATED : February 15, 2005
INVENTOR(S) : Roland Thewes It is certified that error appears in the above-identified patent and that said Letters Patent is hereby corrected as shown below:

On the title page, item [30] (3) Foreign Application Priority Data, please add the following priority claim:

-- May 12, 2000 (DE)  100 23 357--

In column 9, line 53, please replace "$V_8$" with --$V_s$--

In column 10, line 56, please replace both instances of "$\leq$" with --$\leq$--; and in line 57, please replace both instances of "$\leq$" with --$\leq$--

Signed and Sealed this

Ninth Day of January, 2007

JON W. DUDAS
*Director of the United States Patent and Trademark Office*